United States Patent
Miyahara (10) Patent No.: US 10,972,707 B2
(45) Date of Patent: Apr. 6, 2021

(54) ENDOSCOPE AND METHOD OF MANUFACTURING ENDOSCOPE

(71) Applicant: OLYMPUS CORPORATION, Tokyo (JP)

(72) Inventor: Hideharu Miyahara, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 38 days.

(21) Appl. No.: 16/517,138

(22) Filed: Jul. 19, 2019

(65) Prior Publication Data

US 2020/0007829 A1 Jan. 2, 2020

Related U.S. Application Data (63) Continuation of application No. PCT/JP2018/001817, filed on Jan. 22, 2018.

(30) Foreign Application Priority Data

Jan. 24, 2017 (WO) .................. PCT/JP2017/002354
Sep. 20, 2017 (WO) .................. PCT/JP2017/033883

(51) Int. Cl.
*A61B 1/00* (2006.01)
*A61B 1/05* (2006.01)
(Continued)

(52) U.S. Cl.
CPC ............... *H04N 7/22* (2013.01); *A61B 1/005* (2013.01); *A61B 1/0011* (2013.01);
(Continued)

(58) Field of Classification Search
CPC ... A61B 1/00013; A61B 1/05; A61B 1/00165; A61B 1/005; A61B 1/00096;
(Continued)

(56) References Cited

U.S. PATENT DOCUMENTS 8,380,075 B2 * 2/2013 Sakigawa ............ G02B 6/4201
398/128
2003/0081911 A1 5/2003 Ide et al.
(Continued)

FOREIGN PATENT DOCUMENTS

EP 2947486 A1 11/2015
EP 3075298 A1 10/2016
(Continued)

OTHER PUBLICATIONS

English translation of WO 2010/103902 A1 (Year: 2010).*
International Search Report dated Feb. 27, 2018 issued in PCT/JP2018/001817.

*Primary Examiner* — Alison Slater
(74) *Attorney, Agent, or Firm* — Scully, Scott, Murphy & Presser, P.C.

(57) ABSTRACT

An endoscope includes an optical module, the optical module including an optical element including a light emitting surface, an external electrode being disposed, out of a first region and a second region obtained by dividing the light emitting surface substantially in half, only in the first region, a wiring board including a first main surface where the optical element and a bonding electrode are disposed, a bonding wire connecting the external electrode and the bonding electrode to each other, a ferrule into which the optical fiber is inserted, a frame including an upper plate where the ferrule is disposed, including a side plate fixed to the first main surface, including an inner section housing the optical element and a side surface including an opening, and a transparent resin disposed in the inner section, wherein the upper plate is inclined at a predetermined inclination angle to the first main surface.

10 Claims, 11 Drawing Sheets

(51) Int. Cl.
*A61B 1/005* (2006.01)
*A61B 1/04* (2006.01)
*G02B 6/42* (2006.01)
*G02B 23/24* (2006.01)
*G02B 23/26* (2006.01)
*H01S 5/022* (2006.01)
*H04N 7/18* (2006.01)
*H04N 7/22* (2006.01)
*H01L 31/0232* (2014.01)
*H04B 10/25* (2013.01)
*A61B 1/045* (2006.01)
*H04N 5/225* (2006.01)

(52) U.S. Cl.
CPC ...... *A61B 1/00013* (2013.01); *A61B 1/00096* (2013.01); *A61B 1/00124* (2013.01); *A61B 1/00165* (2013.01); *A61B 1/045* (2013.01); *G02B 6/424* (2013.01); *G02B 6/4212* (2013.01); *G02B 23/2446* (2013.01); *G02B 23/2484* (2013.01); *H04N 5/2253* (2013.01); *H04N 5/2254* (2013.01); *H04N 5/2256* (2013.01); *H04N 7/183* (2013.01)

(58) Field of Classification Search
CPC ......... A61B 1/0011; A61B 1/012; A61B 1/00; A61B 1/00126; A61B 1/0017; A61B 1/00117; A61B 1/00167; A61B 1/06; A61B 1/07; A61B 90/361; A61B 1/00124; A61B 1/045; A61B 1/051; G02B 6/4202; G02B 23/2484; G02B 23/2469; G02B 6/424; G02B 23/26; G02B 6/4259; G02B 6/4281; G02B 6/42; G02B 6/423; G02B 6/4243; G02B 6/4257; G02B 6/428; G02B 6/262; G02B 23/2446; G02B 6/4212; H04N 2005/2255; H04N 5/2256; H04N 5/2253; H04N 7/183; H04N 7/22; H04N 5/2254; H04N 5/2251; H01S 5/02284; H01S 5/00252
See application file for complete search history.

(56) References Cited

U.S. PATENT DOCUMENTS

| 2011/0000519 | A1* | 1/2011 | West | F24S 25/67 |
| | | | | 136/244 |
| 2013/0169775 | A1* | 7/2013 | Ono | A61B 1/128 |
| | | | | 348/68 |
| 2014/0236194 | A1* | 8/2014 | Deutsch | A61B 17/062 |
| | | | | 606/148 |
| 2015/0086162 | A1* | 3/2015 | Miyahara | G02B 23/2446 |
| | | | | 385/33 |
| 2015/0318924 | A1 | 11/2015 | Motohara | |
| 2016/0246049 | A1* | 8/2016 | Sakai | G02B 23/2423 |
| 2016/0262599 | A1 | 9/2016 | Nakagawa | |
| 2017/0315310 | A1 | 11/2017 | Nakagawa | |

FOREIGN PATENT DOCUMENTS

| JP | H11-44831 A | A | 2/1999 | | |
| JP | 2001-281503 | A | 10/2001 | | |
| JP | 2009-244702 | A | 10/2009 | | |
| JP | 2010-219166 | A | 9/2010 | | |
| JP | 2013-025092 | A | 2/2013 | | |
| JP | 2014-137584 | A | 7/2014 | | |
| JP | 2015-68835 | A | 4/2015 | | |
| JP | 2015-97588 | A | 5/2015 | | |
| JP | 2015-097589 | A | 5/2015 | | |
| JP | 2015-104387 | A | 6/2015 | | |
| JP | 2016-099467 | A | 5/2016 | | |
| WO | WO-2010103902 | A1 * | 9/2010 | ........... | H01L 33/508 |
| WO | WO 2014/112461 | A1 | 7/2014 | | |
| WO | WO-2015072225 | A1 * | 5/2015 | ......... | G02B 23/2476 |
| WO | WO 2015/079780 | A1 | 6/2015 | | |
| WO | WO 2016/117121 | A1 | 7/2016 | | |
| WO | WO 2016/189691 | A1 | 12/2016 | | |
| WO | WO-2018139406 | A1 * | 8/2018 | ............... | A61B 1/00 |

* cited by examiner

ENDOSCOPE AND METHOD OF MANUFACTURING ENDOSCOPE

CROSS REFERENCE TO RELATED APPLICATION

This application is a continuation application of PCT/JP2018/001817 filed on Jan. 22, 2018 and claims benefit of International Application No. PCT/JP2017/002354 filed on Jan. 24, 2017 and No. PCT/JP2017/033883 filed on Sep. 20, 2017, the entire contents of each of which are incorporated herein by their reference.

BACKGROUND OF THE INVENTION

1. Field of the Invention

The present invention relates to an endoscope including an optical module, in which a bonding wire is bonded to an external electrode in an optical element, disposed in a distal end section, and a method for manufacturing the endoscope.

2. Description of the Related Art

An endoscope includes an image pickup device such as a CMOS image sensor or a CCD in a distal end section in an elongated insertion section. In recent years, an image pickup device having a large number of pixels has been considered to display a high-quality image. When the image pickup device having a large number of pixels is used, an amount of an image signal to be transmitted to a signal processor from the image pickup device increases. Accordingly, in electric signal transmission via a metal wiring by an electric signal, a wire diameter of the metal wiring needs to be increased to transmit a required signal amount, so that the insertion section may be thick due to the wiring.

To reduce a diameter of the insertion section to make the endoscope minimally invasive, optical signal transmission via a thin optical fiber by an optical signal instead of the electric signal is preferable. For the optical signal transmission, an E/O-type optical module (electrical/optical converter) configured to convert an electric signal into an optical signal and an O/E-type optical module (optical/electrical converter) configured to convert an optical signal into an electric signal have been used.

Japanese Patent Application Laid-Open Publication No. 2013-025092 discloses an optical module including an optical element, a substrate on which the optical element is mounted, and a holding section (ferrule) having a through hole into which an optical fiber configured to transmit an optical signal to be inputted into or outputted from the optical element is inserted.

Japanese Patent Application Laid-Open Publication No. 2015-97589 discloses an endoscope in which no stress is applied to an optical fiber even if a bending section is deformed because the optical fiber is inserted through a center of the bending section.

Japanese Patent Application Laid-Open Publication No. 2001-281503 discloses an optical module in which multiple reflection is prevented by arranging an optical element in an inclined manner at a predetermined inclination angle to a bottom surface of a ferrule as a supporting member in the optical fiber. A convex-shaped angle holding member is disposed in the optical element only to arrange the optical element in an inclined manner.

Japanese Patent Application Laid-Open Publication No. 2010-219166 discloses an opening portion or a notch portion into which a bonding wire protrudes is formed in a wavelength converting member disposed on an optical element.

SUMMARY OF THE INVENTION

An endoscope according to an aspect of the present invention is an endoscope including an image pickup device configured to shoot an object and output an image pickup signal and an optical module configured to convert the image pickup signal into an optical signal and transmit the optical signal using an optical fiber in a distal end section in an insertion section, in which the optical module includes a light emitting element which includes a light emitting surface for outputting the optical signal and a rear surface, an external electrode being disposed, out of a first region and a second region obtained by dividing the light emitting surface substantially in half, only in the first region, a wiring board which includes a first main surface and a second main surface, the light emitting element and a bonding electrode being disposed on the first main surface, a bonding wire which connects the external electrode and the bonding electrode to each other, a ferrule which includes an insertion hole, the optical fiber being inserted into the insertion hole, a frame which includes an upper plate and a side plate, the ferrule being disposed on the upper plate and the side plate being fixed to the first main surface in the wiring board, and which includes an inner section housing the light emitting element and a side surface including an opening, and a transparent resin disposed in the inner section in the frame, in which the upper plate is inclined at a predetermined inclination angle to the first main surface, and a first distance from the first main surface to the first region is longer than a second distance from the first main surface to the second region.

A method for manufacturing an endoscope according to another aspect of the present invention is a method in which a light emitting element which includes a light emitting surface for outputting an optical signal and a rear surface opposing the light emitting surface, an external electrode being disposed, out of a first region and a second region obtained by dividing the light emitting surface substantially in half, only in the first region is disposed, in a wiring board including a first main surface and a second main surface, on the first main surface on which a bonding electrode is disposed, the external electrode and the bonding electrode are connected to each other with a bonding wire, a frame which includes an upper plate and a side plate, includes a side surface including an opening, and is inclined to the first main surface is disposed on the first main surface in the wiring board such that a first distance from the first main surface to the first region is longer than a second distance from the first main surface to the second region and the light emitting element is housed in an inner section, a ferrule is disposed on the upper plate, an optical fiber configured to transmit the optical signal is inserted into an insertion hole in the ferrule, and a transparent resin is injected into the inner section from the opening in the frame.

DETAILED DESCRIPTION OF THE PREFERRED EMBODIMENT(S)

First Embodiment

Figure 1:
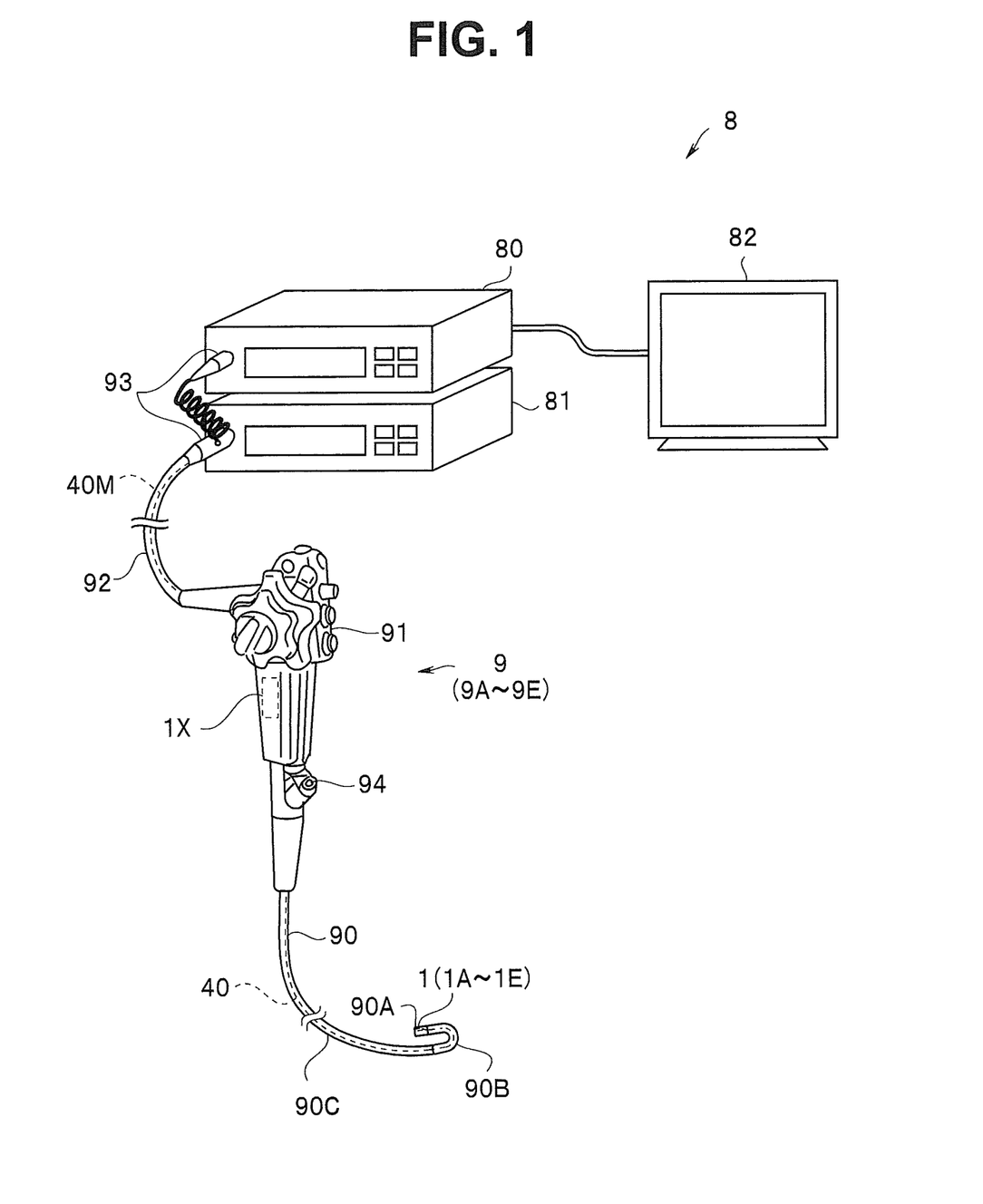
FIG. 1 is a perspective view of an endoscope system including an endoscope according to a first embodiment.

An endoscope system 8 including an endoscope 9 according to the present embodiment illustrated in FIG. 1 includes the endoscope 9, a processor 80, a light source device 81, and a monitor 82. For example, the endoscope 9 shoots an in-vivo image of a subject and outputs an image pickup signal with an insertion section 90 circular in cross section inserted into a body cavity of the subject.

Note that in the following description, drawings based on each of embodiments are schematic and a relationship between a thickness and a width of each of sections and a ratio of the thicknesses of the sections respectively differ from actual ones, and sections which differ in dimensional relationship or ratio may also be included among the drawings. Illustration of some of components and assignment of reference numerals may be omitted.

An operation section 91 provided with various types of buttons configured to operate the endoscope 9 is disposed in a proximal end portion of the insertion section 90 in the endoscope 9. The operation section 91 has a treatment instrument insertion opening in a channel 94 (see FIG. 2) configured to insert living body forceps, electrocautery, an inspection probe, and the like into the body cavity of the subject.

The insertion section 90 includes a rigid distal end section 90A, a bendable bending section 90B consecutively connected to the distal end section 90A, and a flexible section 90C consecutively connected to the bending section 90B. The bending section 90B is bent by an operation of the operation section 91.

A universal code 92 extending from the operation section 91 is connected to the processor 80 and the light source device 81 via a connector 93. A signal cable 40M configured to transmit an electric signal to be outputted by an O/E-type optical module 1X is inserted through the universal code 92. Note that the optical module 1X may be arranged in the connector 93 in the universal code 92, for example.

The processor 80 controls the entire endoscope system 8 while performing signal processing for an image pickup signal to be outputted by an image pickup apparatus 3 (see FIG. 3) and outputting the image pickup signal as an image signal. The monitor 82 displays the image signal to be outputted by the processor 80.

The light source device 81 includes a white LED, for example. Illumination light to be emitted by the light source device 81 is guided to an illumination optical system 96 (see FIG. 2) in the distal end section 90A via a light guide (not illustrated) configured to be inserted through the universal code 92 and the insertion section 90, to illuminate an object.

The image pickup apparatus 3 including an E/O-type optical module 1 (see FIGS. 3 to 7) is disposed in the distal end section 90A. In the endoscope 9, an electric signal is converted into an optical signal by the optical module 1 in the rigid distal end section 90A, and is transmitted to the operation section 91 via a thin optical fiber 40 configured to be inserted through the insertion section 90. The optical signal is converted again into an electric signal by the O/E-type optical module 1X disposed in the operation section 91, and is transmitted to an electrical connector 93 via a signal cable 40M as a metal wiring configured to be inserted through the universal code 92.

The image pickup signal is transmitted via the optical fiber 40 within the insertion section 90 having a small diameter, and is transmitted via the signal cable 40M as a thicker metal wiring than the optical fiber 40 within the universal code 92 which is not inserted into a body and an outer diameter of which is hardly restricted.

Note that if the optical module 1X is arranged in the connector 93 or the processor 80, the optical fiber 40 is inserted through the universal code 92.

Figure 2:
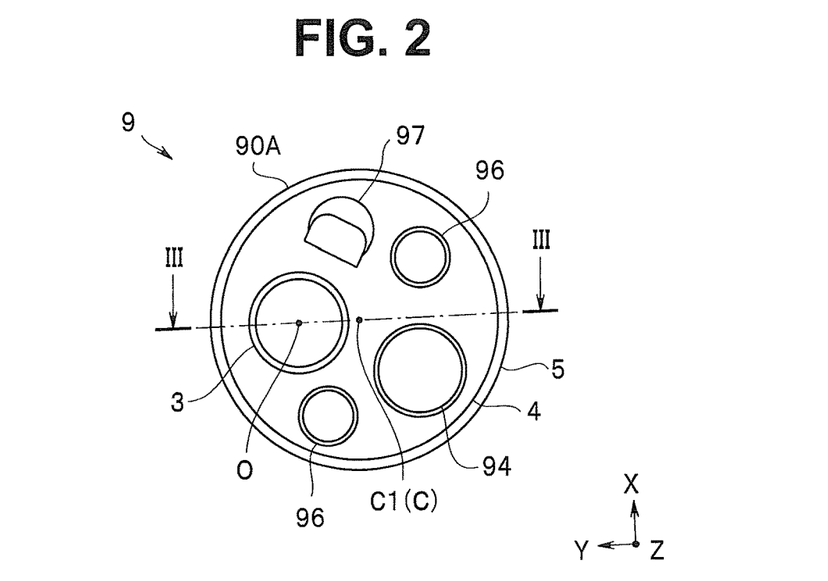
FIG. 2 is a plan view of a distal end section in the endoscope according to the first embodiment.

FIG. 2 is a front view of the distal end section 90A in the endoscope 9 as viewed in a distal end direction. The distal end section 90A includes a cylindrical housing 4, which is tubular in its rear, an outer peripheral surface of which is covered with an outer skin 5 made of a resin. The housing 4 has a plurality of through holes parallel to a distal end section central axis C1 of the distal end section 90A.

An observation window of the image pickup optical system 2A and an opening of the channel 94 are disposed on a distal end surface such that the distal end section central axis C1 (a central axis C of the insertion section 90) is interposed therebetween. In other words, an optical axis O of the image pickup optical system 2A inserted into the through hole of the housing 4 is parallel to the distal end section central axis C1 (C) and is eccentric.

Respective illumination windows of the two illumination optical systems 96 and a nozzle 97 for air feeding/water feeding are further disposed on the distal end surface.

Figure 3:
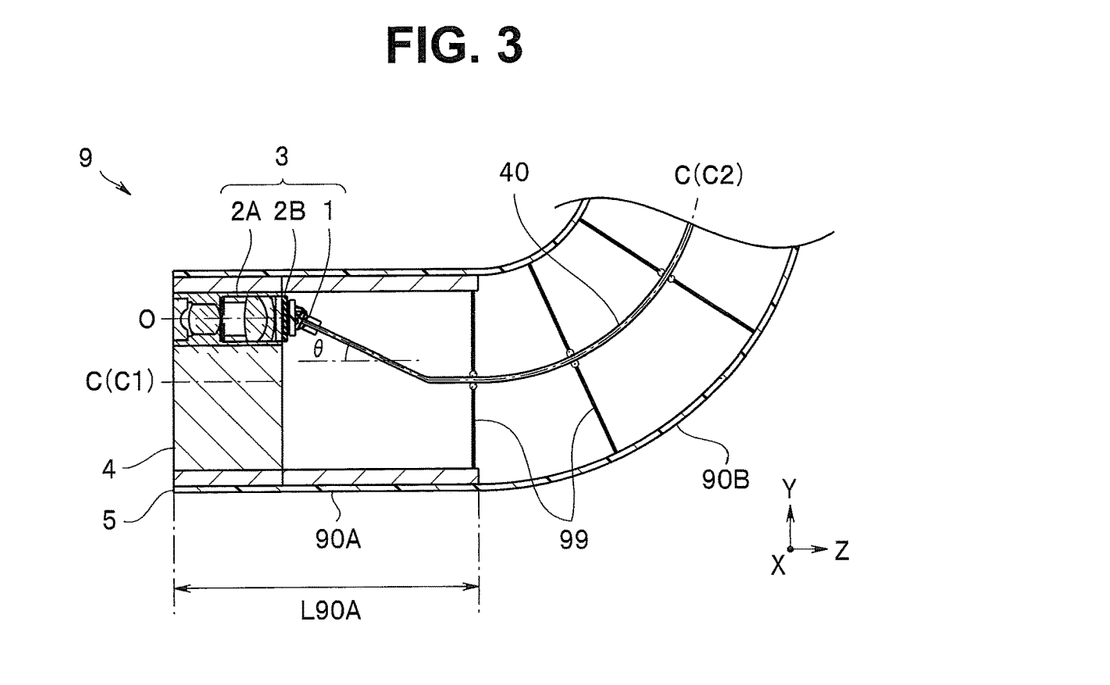
FIG. 3 is a cross-sectional view along a line III-III illustrated in FIG. 2 of the distal end section in the endoscope according to the first embodiment.

FIG. 3 illustrates a plane (YZ plane) including the optical axis O of the image pickup optical system 2A and the distal end section central axis C, as indicated by a line illustrated in FIG. 2.

The image pickup apparatus 3 including the image pickup optical system 2A, an image pickup device 2B, and the optical module 1 is housed in the through hole of the housing 4 in the distal end section 90A having a length L90A.

The image pickup device 2B configured to shoot an object and output an image pickup signal is a CMOS image sensor or a CCD. The image pickup signal is converted into an optical signal in the optical module 1, The optical fiber 40 in the optical module 1 includes a core having a diameter of 50 μm configured to transmit light and a clad having a diameter of 125 μm which covers an outer periphery of the core, for example. The optical fiber 40 extends toward the distal end section central axis C1, and is arranged along a bending section central axis C2 of the bending section 90B.

In other words, guide members 99 for arranging the optical fiber 40 along the distal end section central axis C1 (the central axis C) are disposed in a proximal end portion of the distal end section 90A and the bending section 90B. Details of the guide members 99 are disclosed in Japanese Patent Application Laid-Open Publication No. 2015-97589 already described. The guide members 99 are also preferably disposed in the flexible section 90C, which are not illustrated. Note that the flexible section 90C is not greatly deformed compared to the bending section 90B. Therefore, an arrangement spacing between the guide members 99 in the flexible section 90C may be longer than an arrangement spacing in the bending section 90B.

One multi-lumen tube having substantially the same outer diameter as an inner diameter of the bending section 90B and inserted through the bending section 90B may be used as the guide member. In other words, when a conduit inserted through a center of the multi-lumen tube allows insertion of the optical fiber 40, the optical fiber 40 can be arranged along the bending section central axis C2.

To the optical fiber 40 inserted through the insertion section 90 in the endoscope 9, a stress is applied when the insertion section 90 is deformed. The optical fiber 40 receives a large stress particularly when the insertion section 90 is deformed by a bending operation of the bending section 90B.

In the endoscope 9, the optical fiber 40 is arranged along the bending section central axis C2. Therefore, even if the bending section 90B is deformed, the optical fiber 40 does not receive a great stress. Accordingly, the endoscope 9 is high in reliability because a loss may hardly occur in a video signal to be transmitted by the optical fiber 40.

Further, as illustrated in FIG. 3, in the optical module 1 in the endoscope 9, the optical fiber 40 is arranged such that a fiber distal end section is inclined by an angle θ, e.g., 45°±10°, i.e., not less than 35 degrees and not more than 55 degrees to the distal end section central axis C1 in a cross section (the YZ plane) including the central axis C and the optical axis O and extends in a direction toward the distal end section central axis C1.

As described above, the endoscope 9 including the image pickup device 2B having a large number of pixels transmits an image signal via the optical fiber 40. Therefore, the endoscope 9 is minimally invasive and can display a high-quality image. The optical fiber 40 can be arranged along the bending section central axis C2 without being greatly bent. Therefore, the endoscope 9 is high in reliability. Further, the optical fiber 40 can be arranged along the bending section central axis C2 in a short distance. Therefore, the endoscope 9 is minimally invasive because the length L90A of the distal end section 90A is small.

Details of the optical module 1 in the endoscope 9 will be described below with reference to FIGS. 4 to 8A.

The optical module 1 includes a wiring board 10, an optical element 20, a bonding wire 30, a ferrule 50, a holding frame 60, and a transparent resin 70.

Figure 4:
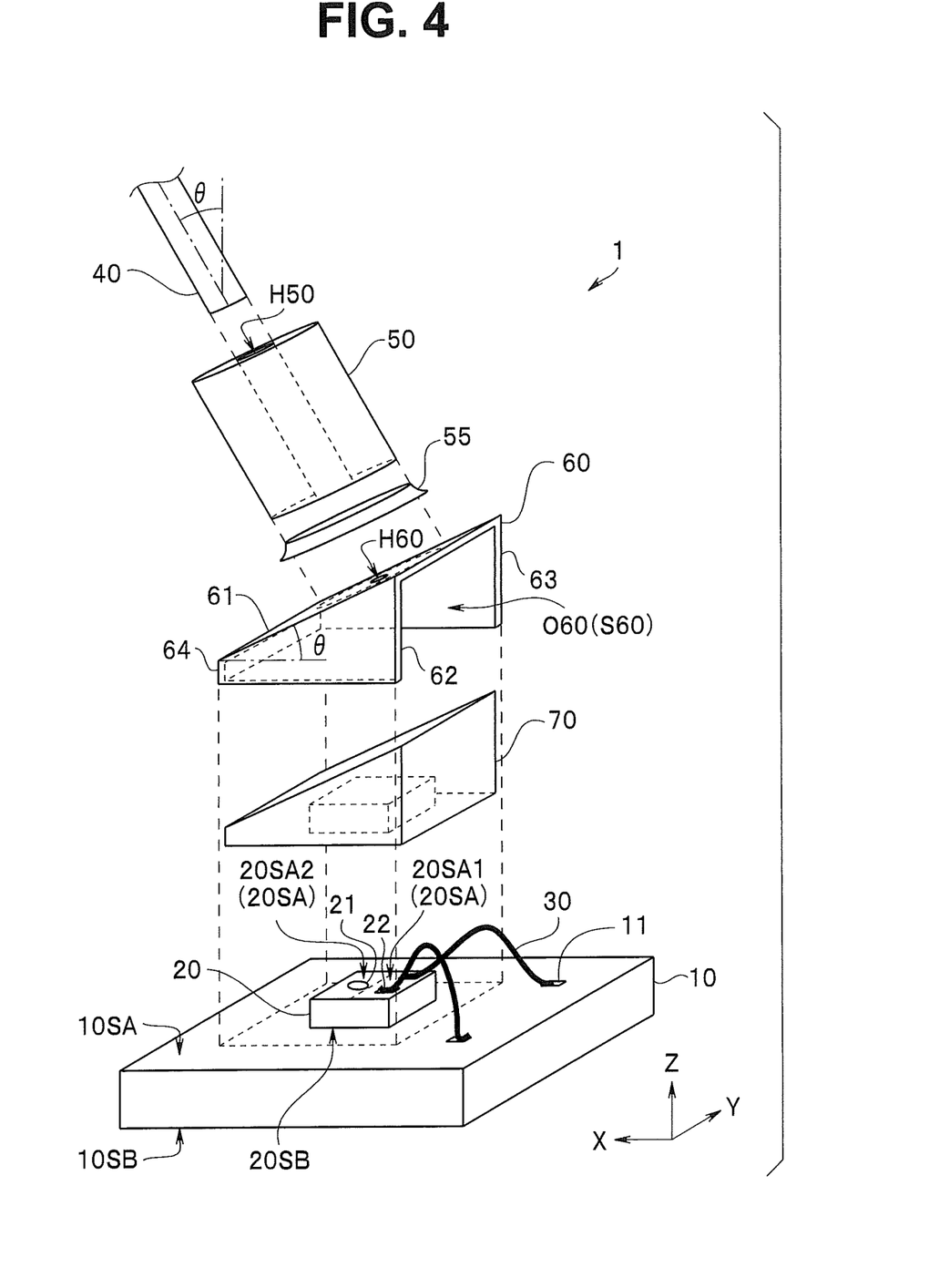
FIG. 4 is an exploded view of an optical module in the endoscope according to the first embodiment.

The wiring board 10 includes a first main surface 10SA and a second main surface 10SB opposing the first main surface 10SA. The optical element 20 and a bonding electrode 11 are disposed on the first main surface 10SA in the wiring board 10. A driving signal is transmitted to the bonding electrode 11 via a wiring not illustrated.

As illustrated in FIG. 3, the image pickup device 2B is mounted on the second main surface 10SB in the wiring board 10 in the optical module 1. Accordingly, the first main surface 10SA and the second main surface 10SB are perpendicular to the optical axis O of the image pickup device 2B. Electronic components such as a driving IC and a chip capacitor for driving the optical element 20 may be mounted on the wiring board 10.

The optical element 20 includes a light emitting surface 20SA for outputting an optical signal and a rear surface 20SB opposing the light emitting surface 20SA. The optical element 20 is a surface light emitting laser chip including a light emitting section 21 configured to output light of the optical signal. For example, a micro optical element 20 having planar-view dimensions (a size in a direction perpendicular to the optical axis) of 250 μm×300 μm and having a thickness of 150 μm includes a light emitting section 21 having a diameter of 20 μm and an external electrode 22 configured to feed a driving signal to the light emitting section 21 on a light emitting surface 20SA.

In the optical element 20, two external electrodes 22 are disposed, out of a first region 20SA1 and a second region 20SA2 obtained by dividing the light emitting surface 20SA substantially in half, only in the first region 20SA1. In other words, the first region 20SA1 and the second region 20SA2 need not be accurately two halves such that their respective areas are completely equal to each other, but may be respectively separated as different regions.

The bonding wire 30 connects the external electrode 22 in the optical element 20 and the bonding electrode 11 in the wiring board 10 to each other. The bonding wire 30 is a metal wire having a diameter of 30 μm, for example. The bonding wire 30 protrudes by approximately 100 μm from the light emitting surface 20SA.

Figure 8A:
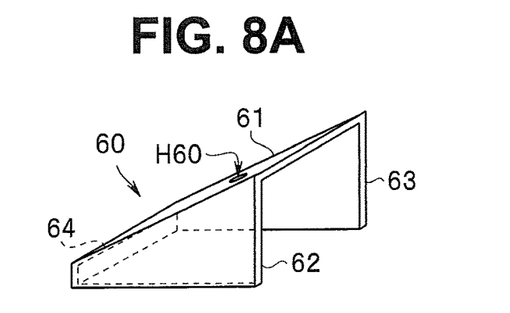
FIG. 8A is a perspective view of a holding frame in the optical module in the endoscope according to the first embodiment.

The holding frame 60 includes an upper plate 61 and a plurality of side plates 62, 63, and 64. The side plates 62, 63, and 64 are fixed to the first main surface 10SA in the wiring board 10. An inner section S60 in the holding frame 60 has a space formed by the upper plate 61 and the side plates 62, 63, and 64. Among four side surfaces, the side surface having a largest area opposing the side plate 64 is an opening O60. The optical element 20 disposed on the wiring board 10 is housed in the inner section S60 in the holding frame 60.

Figure 5:
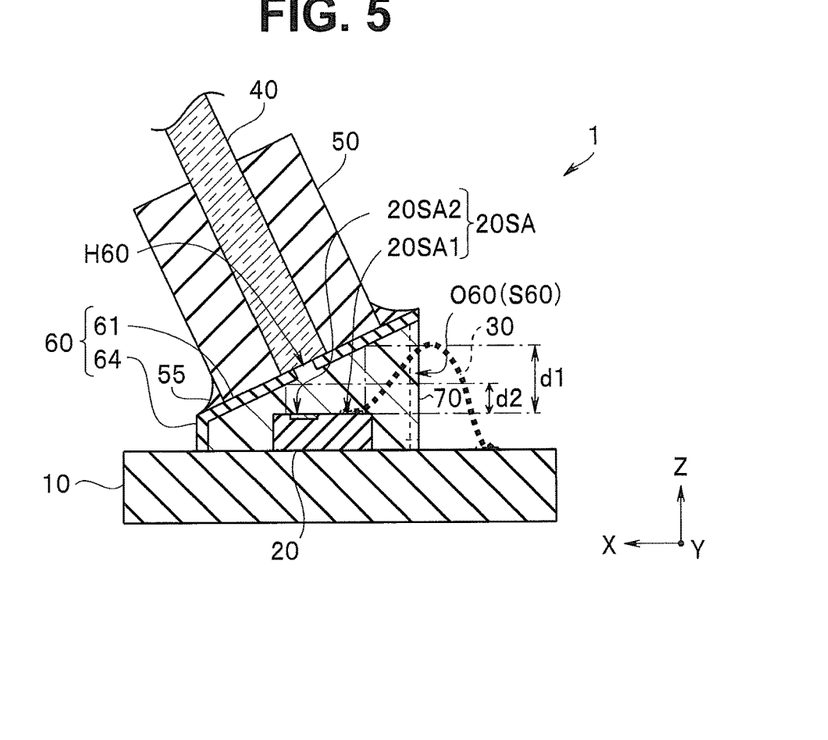
FIG. 5 is a cross-sectional view of the optical module in the endoscope according to the first embodiment.
Figure 6:
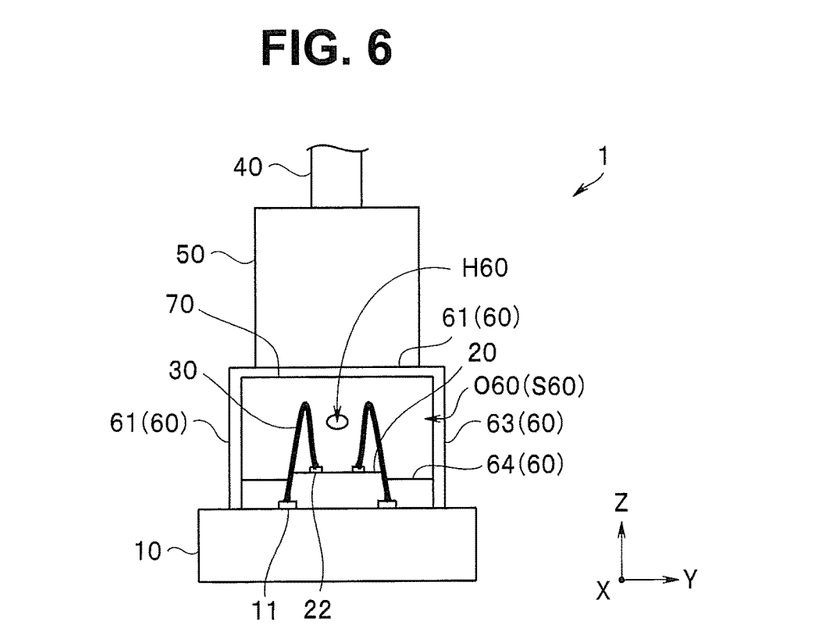
FIG. 6 is a side view of the optical module in the endoscope according to the first embodiment.
Figure 7:
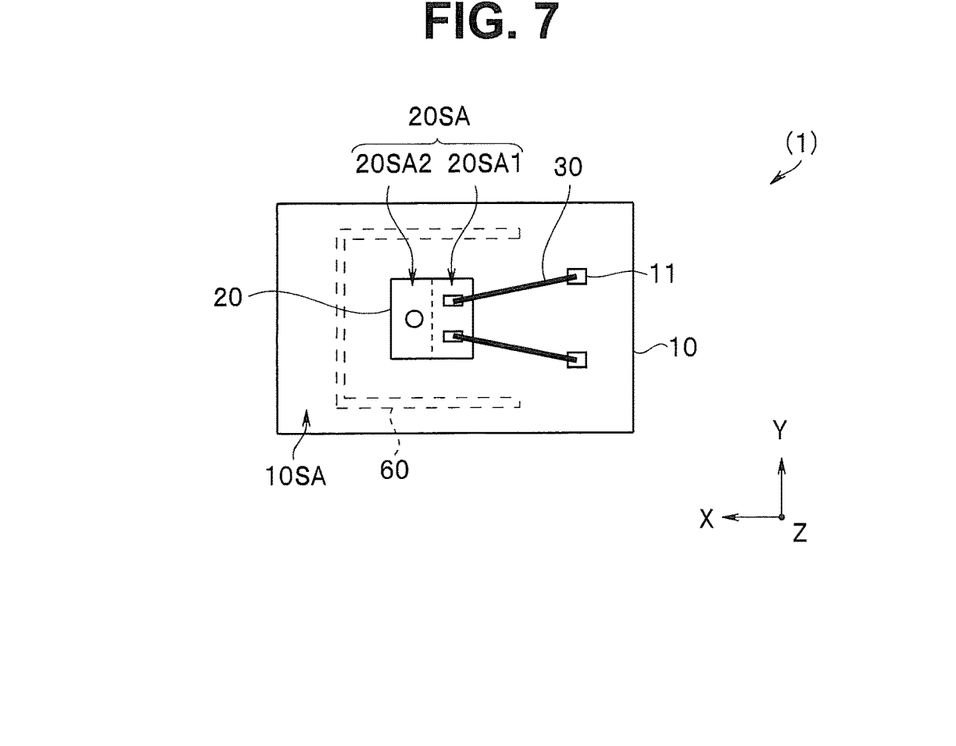
FIG. 7 is a top view of the optical module in the endoscope according to the first embodiment.

The upper plate 61 in the holding frame 60 is inclined at a predetermined inclination angle θ to the first main surface 10SA in the wiring board 10. In other words, as illustrated in FIG. 5, the upper plate 61 is inclined such that a first distance d1 from the first main surface 10SA to the first region 20SA1 is longer than a second distance d2 from the first main surface 10SA to the second region 20SA2.

As already described, the bonding wire 30 protrudes by approximately 100 μm from the light emitting surface 20SA. However, the upper plate 61 is inclined. Therefore, the bonding wire 30 does not contact the upper plate 61. Accordingly, even if the upper plate 61 is a conductor, conduction do not occur between the two bonding wires 30.

Even if the upper plate 61 is a nonconductor, for example, a resin or ceramic, when the holding frame 60 is disposed on the wiring board 10, the bonding wire 30 is deformed upon being pressed by the upper plate 61 so that no stress is applied to a bonding section. Accordingly, bonding reliability is ensured in the optical module 1.

Note that if the bonding wire 30 contacts the upper plate 61 but is not greatly deformed, bonding reliability may be ensured in the optical module 1. However, the bonding wire 30 does not preferably contact the upper plate 61.

Since the upper plate 61 is inclined, a length from the first main surface 10SA in the wiring board 10 to an upper surface of the ferrule 50 in the optical module 1 is smaller than a length in an optical module in which an upper plate 61 is not inclined. In other words, a length in an optical axis direction of the optical module 1 is small. Therefore, the endoscope 9 is minimally invasive because a length of the rigid distal end section 90A is small.

The transparent resin 70 is disposed in the inner section S60 in the holding frame 60. The transparent resin 70 is a refractive index matching material having substantially the same refractive index as a refractive index of the core in the optical fiber 40. Examples of the transparent resin 70 include an acrylic-based resin, an epoxy-based resin, a vinyl-based resin, an ethylene-based resin, a silicone-based resin, a urethane-based resin, a polyamide-based resin, a fluorine-based resin, a polybutadiene-based resin, and a polycarbonate-based resin. Among the resins, the acrylic-based resin and the epoxy-based resin are appropriate for the transparent resin 70 from a viewpoint of moisture resistance, heat resistance, detachment resistance, and impact resistance.

Note that in the transparent resin 70 illustrated in FIG. 4, a space corresponding to the optical element 20 is illustrated and a space corresponding to the bonding wire 30 is not illustrated.

Although the holding frame 60 includes side plates 62, 63, and 64, a surface, opposing the side plate 64, of the holding frame 60 does not include a side plate but is an opening O60. The transparent resin 70 is injected in a liquid state into the inner section S60 from the opening O60 after the holding frame 60 is fixed to the wiring board 10, and is solidified by curing treatment, e.g., heating or ultraviolet irradiation.

The ferrule 50 is fixed to the upper plate 61 in the holding frame 60 using an adhesive 55. The ferrule 50 is made of glass, a metal member, ceramic, or silicon. An inner wall shape of an insertion hole H50 in the ferrule 50 may be prismatic in addition to being columnar if the optical fiber 40 can be held in a wall surface of the insertion hole H50.

A fiber distal end portion of the optical fiber 40 is inserted into the insertion hole 50H in the ferrule 50, and is optically coupled to the optical element 20. In other words, the upper plate 61 in the holding frame 60 includes a through hole H60 as an optical path.

A depth direction of the insertion hole 50H is perpendicular to a bottom surface of the ferrule 50. Accordingly, the fiber distal end portion of the optical fiber 40 is disposed perpendicularly to the upper plate 61 in the holding frame 60 when inserted into the insertion hole 50H.

The upper plate 61 is inclined at an inclination angle θ to the first main surface 10SA in the wiring board 10. Therefore, the optical fiber 40 extends toward the distal end section central axis C1 at an inclination angle θ of not less than 35 degrees and not more than 55 degrees, for example. In other words, the optical module 1 is arranged at a position eccentric from the central axis C1 of the distal end section 90A and a position where the second region 20SA2 is closer to the distal end section central axis C1 than the first region 20SA1, and the optical fiber 40 extending toward the distal end section central axis C1 is inserted through a center of the bending section 90B along the bending section central axis C2. Accordingly, in the endoscope 9, the optical fiber 40 can be arranged along the bending section central axis C2 in a short distance. Therefore, the endoscope 9 is minimally invasive because the length L90A of the distal end section 90A is small.

<Method for Manufacturing Endoscope (Optical Module)>

Figure 9:
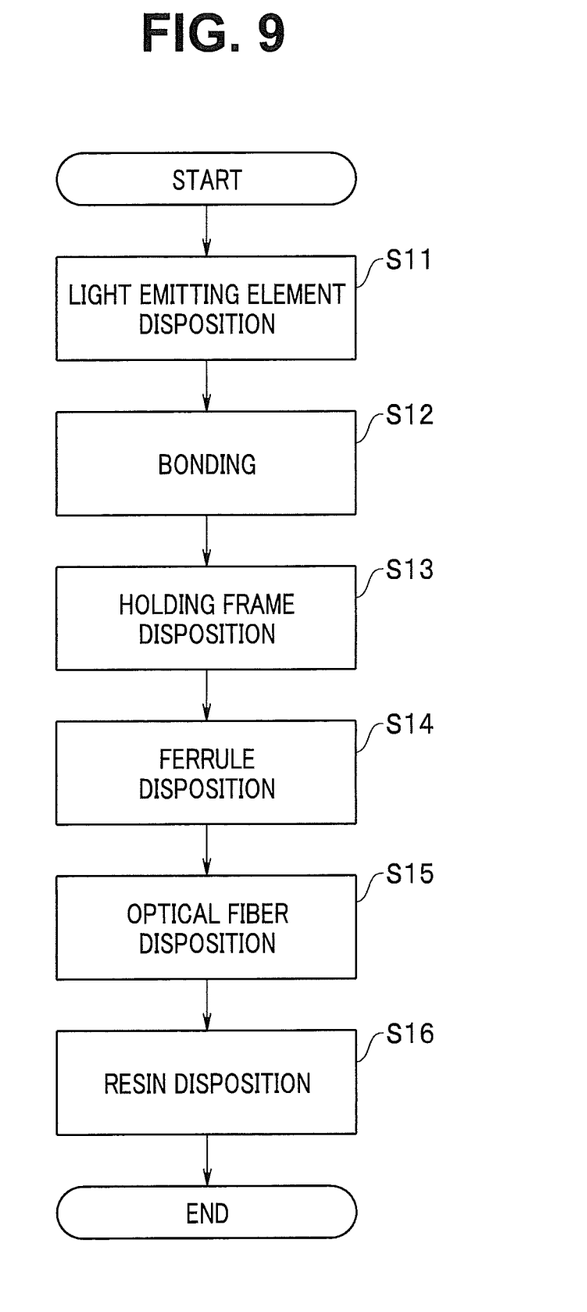
FIG. 9 is a flowchart for describing a method for manufacturing the optical module in the endoscope according to the first embodiment.

A method for manufacturing the optical module 1 in the endoscope 9 will be simply described with reference to a flowchart illustrated in FIG. 9.

<Step S11> Light Emitting Element Disposition Process

The optical element 20 is disposed on the first main surface 10SA in the wiring board 10 with an adhesive, for example.

<Step S12> Bonding Process

The external electrode 22 in the optical element 20 and the bonding electrode 11 in the wiring board 10 are connected to each other with the bonding wire 30. The bonding wire 30 protrudes by approximately 100 μm from the light emitting surface 20SA to ensure bonding reliability.

<Step S13> Holding Frame Disposition Process

The holding frame 60 is disposed on the first main surface 10SA in the wiring board 10 such that the optical element 20 is housed in the inner section S60. The upper plate 61 in the holding frame 60 is inclined to the first main surface 10SA. Accordingly, the bonding wire 30 is not deformed.

<Step S14> Ferrule Disposition Process

The ferrule 50 is disposed on the upper plate 61.

<Step S15> Optical Fiber Disposition Process

The fiber distal end portion of the optical fiber 40 configured to transmit an optical signal is inserted into and fixed to the insertion hole H50 in the ferrule 50.

<Step S16> Resin Disposition Process

The liquid-like and uncured transparent resin 70 is injected into the inner section S60 in the holding frame 60 via the opening O60, and is further subjected to curing treatment. Since the side surfaces of the holding frame 60 has the opening O60, the transparent resin 70 can be easily injected into the inner section S60.

If at least a space between the light emitting surface 20SA and the optical fiber 40 is filled with the transparent resin 70, the inner section S60 need not be completely filled with the transparent resin 70. Contrary to this, a part of the transparent resin 70 may spread to the outside of the holding frame 60. An outer surface of the optical module 1 may be covered with light shielding resin.

Note that the optical fiber disposition process S15 may be performed after the resin disposition process S16. The optical module 1 and the like are disposed in the distal end section 90A, to complete the endoscope 9.

According to the above-described manufacturing method, there can be provided a minimally invasive endoscope high in reliability and configured to display a high-quality image.

Figure 8B:
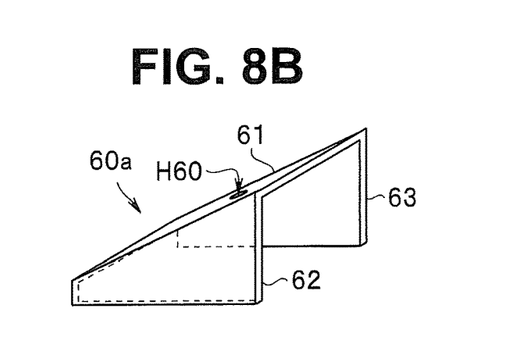
FIG. 8B is a perspective view of the holding frame in the optical module in the endoscope according to the first embodiment.
Figure 8C:
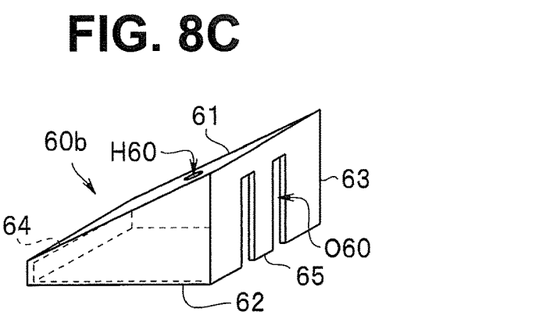
FIG. 8C is a perspective view of the holding frame in the optical module in the endoscope according to the first embodiment.
Figure 8D:
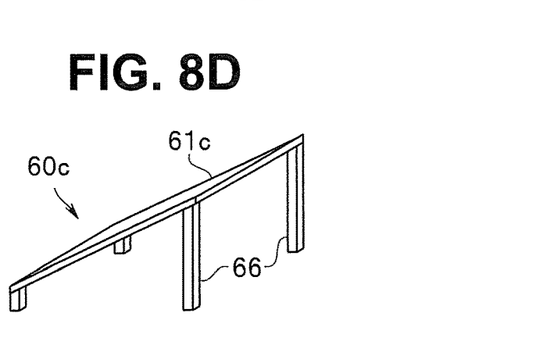
FIG. 8D is a perspective view of the holding frame in the optical module in the endoscope according to the first embodiment.

Note that the optical module 1 may include holding frames 60a, 60b, and 60c respectively illustrated in FIGS. 8B, 8C, and 8D.

The holding frame 60a illustrated in FIG. 8B does not include the side plate 64. The upper plate 61 is held by the two side plates 62 and 63. Note that if the upper plate 61 can be stably held, a holding frame including only one side plate may be used. In other words, a holding frame may include at least one side plate.

The holding frame 60b illustrated in FIG. 8C includes a side plate 65 opposing the side plate 64. The side plate 65 has two openings O60. A part of the bonding wire 30 protrudes outward from the holding frame 60b via the opening O60, which is not illustrated. Since the opening O60 is like a slit, the holding frame 60b can be disposed on the first main surface 10SA on which the bonding wire 30 is disposed not to contact the bonding wire 30.

The holding frame 60c illustrated in FIG. 8D includes four columns 66 which have a similar effect to an effect of a side plate and can be regarded as the side plate. If an upper plate 61c is made of a transparent material, there may be no through hole. Further, the upper plate 61c and the columns 66 are respectively separate members.

As described above, the holding frame can be subjected to various modifications if the inner section can house the light emitting element and the upper plate inclined such that the bonding wire is not deformed is stably held.

Endoscopes 9A to 9E according to embodiments described below respectively have similar effects to the effect of the endoscope 9 according to the first embodiment, and hence components having the same functions are respectively assigned the same reference numerals, to omit description of the components.

Second Embodiment

Figure 10:
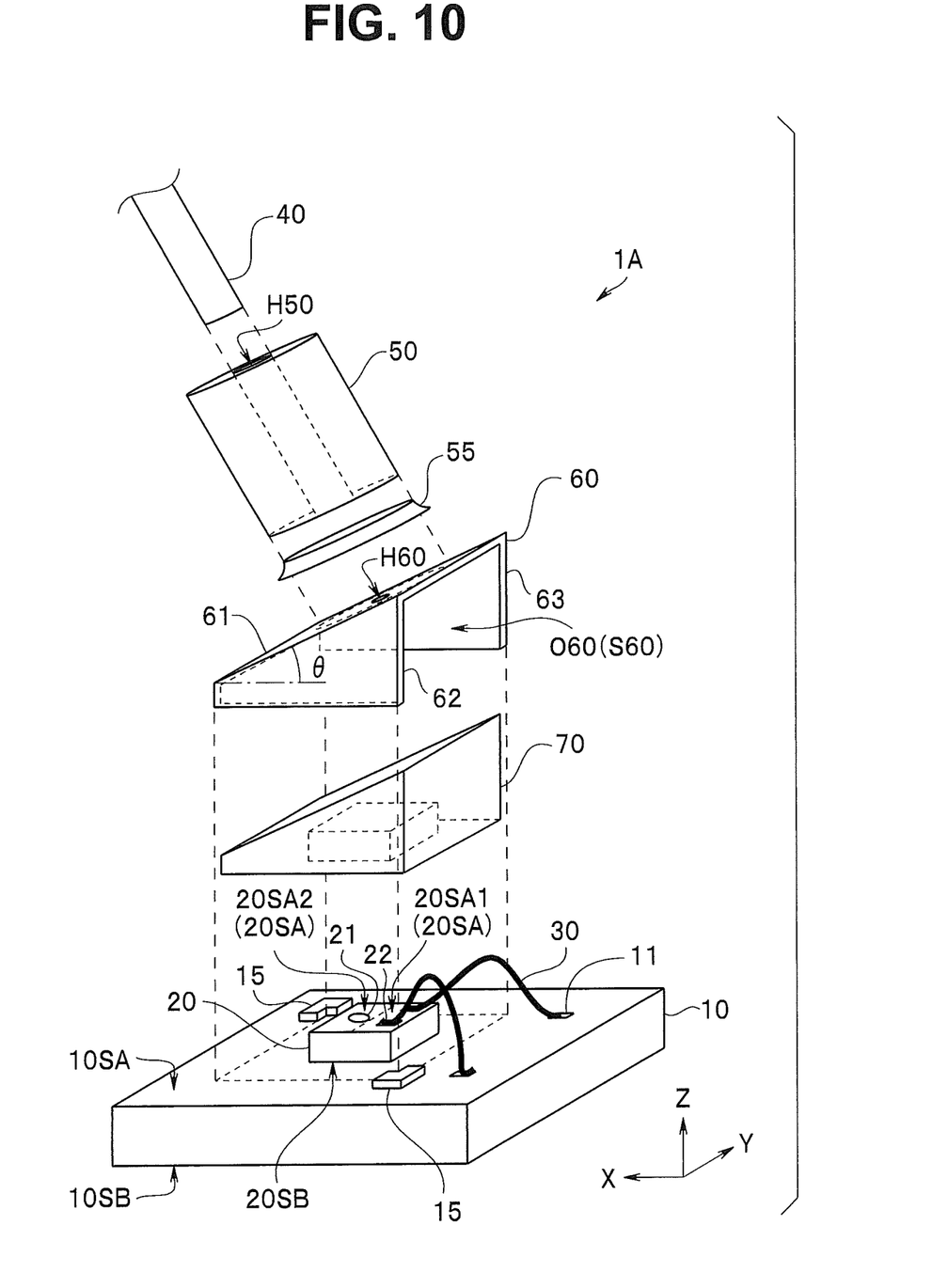
FIG. 10 is an exploded view of an optical module in an endoscope according to a second embodiment.

An endoscope 9A according to the present embodiment includes an optical module 1A illustrated in FIG. 10. In the optical module 1A, two position defining members 15 as first members configured to define a position of a holding frame 60 on a first main surface 10SA in a wiring board 10 are disposed on the first main surface 10SA.

A position in an in-plane (XY plane) direction of the holding frame 60 is defined when corner portions of side plates 62 and 63 respectively abut on wall surfaces of the position defining members 15. Note that if the two wall surfaces perpendicular to each other of the position defining members 15 each having an L shape are sufficiently long, either one of the position defining members 15 can also accurately define the position in the in-plane direction of the holding frame 60. In other words, the optical module 1A may include at least one position defining member 15.

In the optical module 1A, the holding frame 60 is more easily positioned than in the optical module 1.

Third Embodiment

Figure 11:
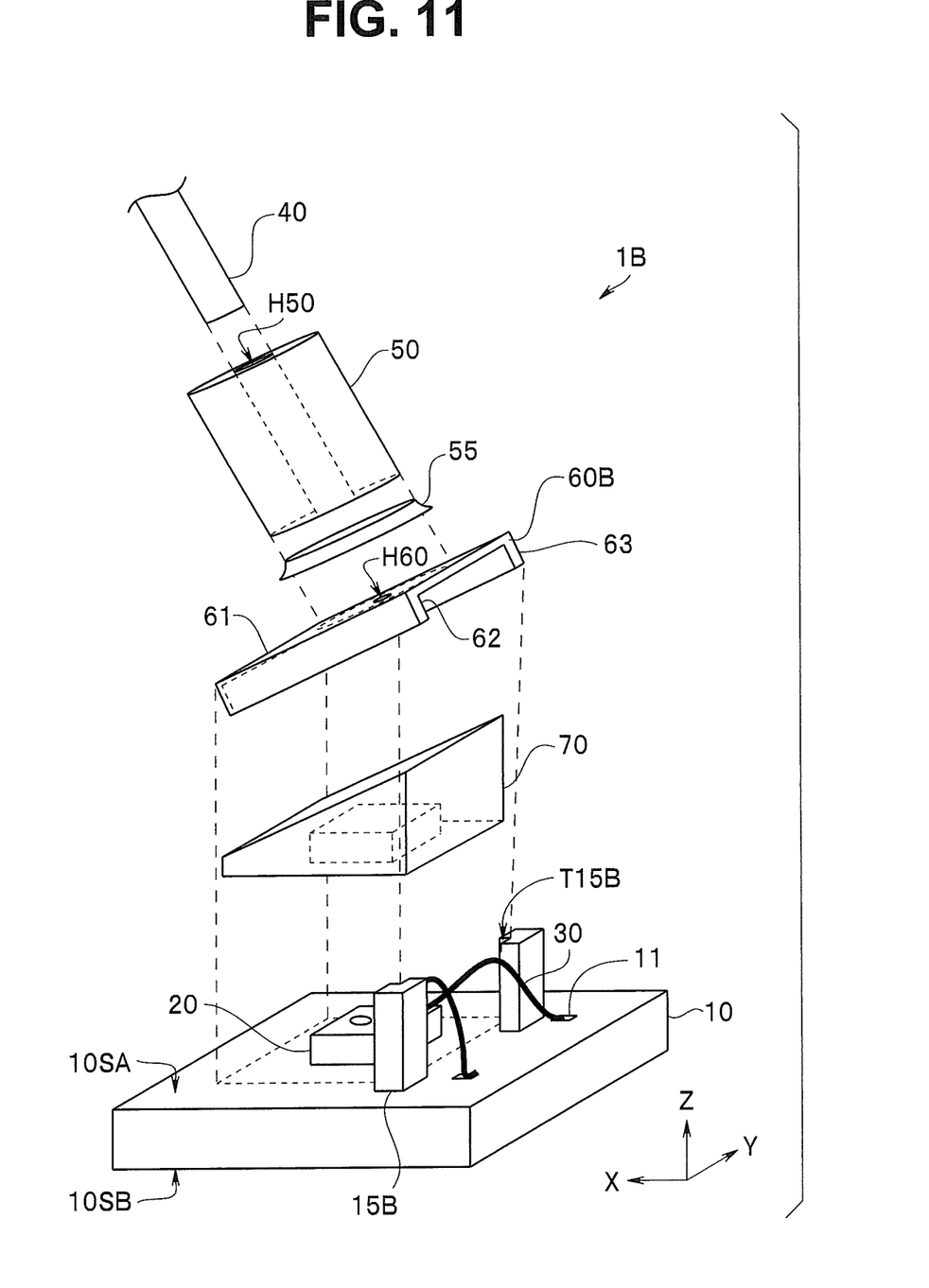
FIG. 11 is an exploded view of an optical module in an endoscope according to a third embodiment.

An endoscope 9B according to the present embodiment includes an optical module 1B illustrated in FIG. 11. In the optical module 1B, two position inclination defining members 15B as third members disposed between side plates 62 and 63 in a holding frame 60B and a first main surface 10SA in a wiring board 10.

The position inclination defining members 15B defines a position of the holding frame 60B in the first main surface 10SA and an inclination angle of an upper plate 61.

In other words, corner portions of the side plates 62 and 63 in the holding frame 60B are respectively fitted in recessed sections (notches) T15B in upper portions of the position inclination defining members 15B. The inclination angle of the upper plate 61 is defined based on a height of the recessed section T15B from the first main surface 10SA.

In the optical module 1B, the holding frame 60B can be accurately disposed at a predetermined angle on the wiring board 10. Not only that, the holding frame 60B is easily manufactured.

Note that the optical module 1B may include, instead of the position inclination defining members 15B, inclination defining members as second members each having no recessed portion and defining an inclination angle when the holding frame 60B abuts on an upper surface of the inclination defining member, unlike the position inclination defining members 15B. The optical module 1B may include at least one position inclination defining member 15B.

Fourth Embodiment

An endoscope 9C according to the present embodiment includes an optical module 1C. In the optical module 1C illustrated in FIG. 12, a first main surface 10SA in a wiring board 10C includes two grooves T10 for defining a position of a holding frame 60C on the first main surface 10SA, and side plates 62C and 63C in the holding frame 60C are respectively fitted in the grooves T10.

Figure 12:
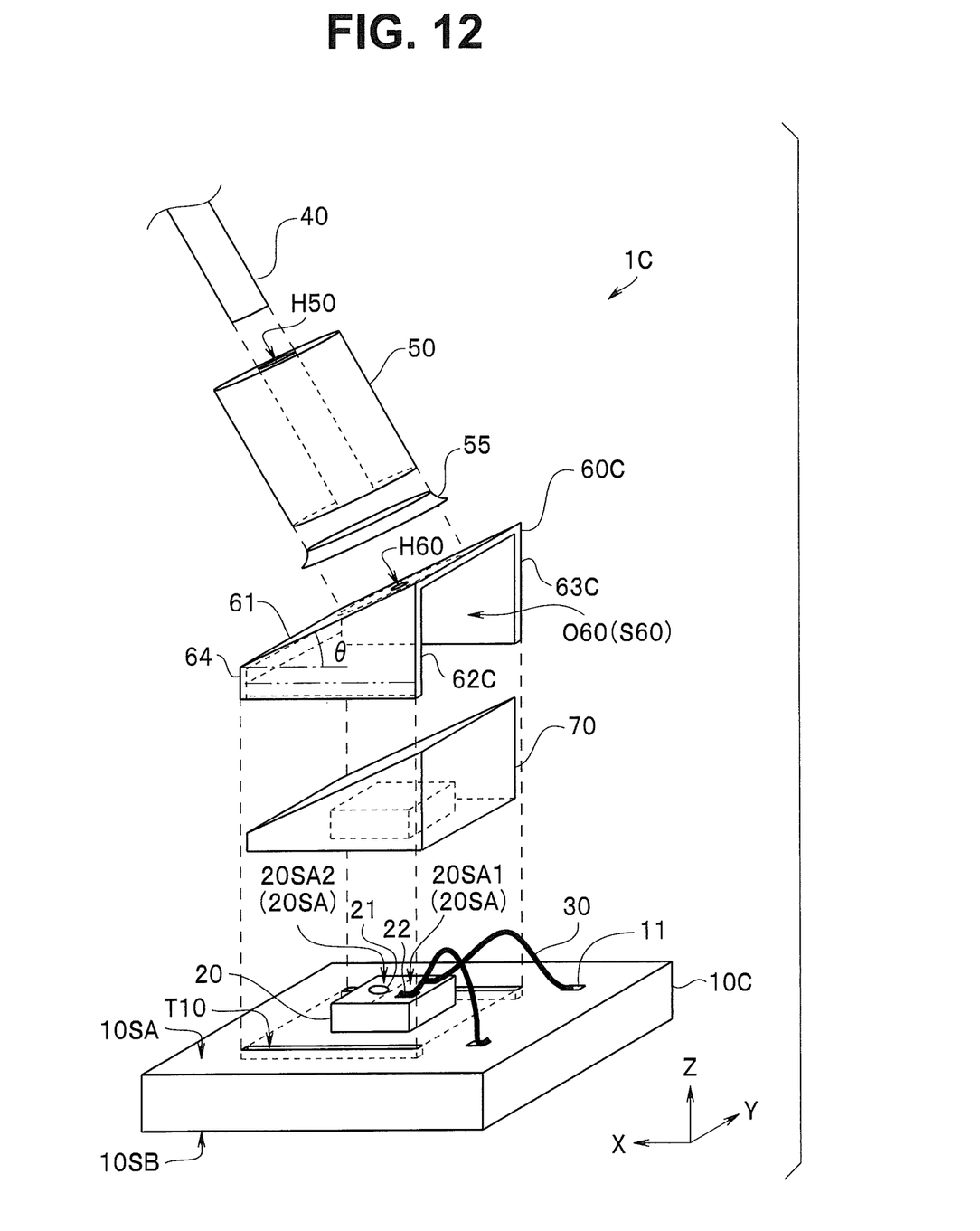
FIG. 12 is an exploded view of an optical module in an endoscope according to a fourth embodiment.

A bottom surface of a side plate 64 abuts on the first main surface 10SA. Note that the first main surface 10SA may include one groove T10, and only the side plate 62C may be fitted in the groove T10. In other words, the wiring board 10C may include at least one groove T10.

In the optical module 1C, the holding frame 60C can be easily and accurately disposed on the wiring board 10.

Fifth Embodiment

Figure 13:
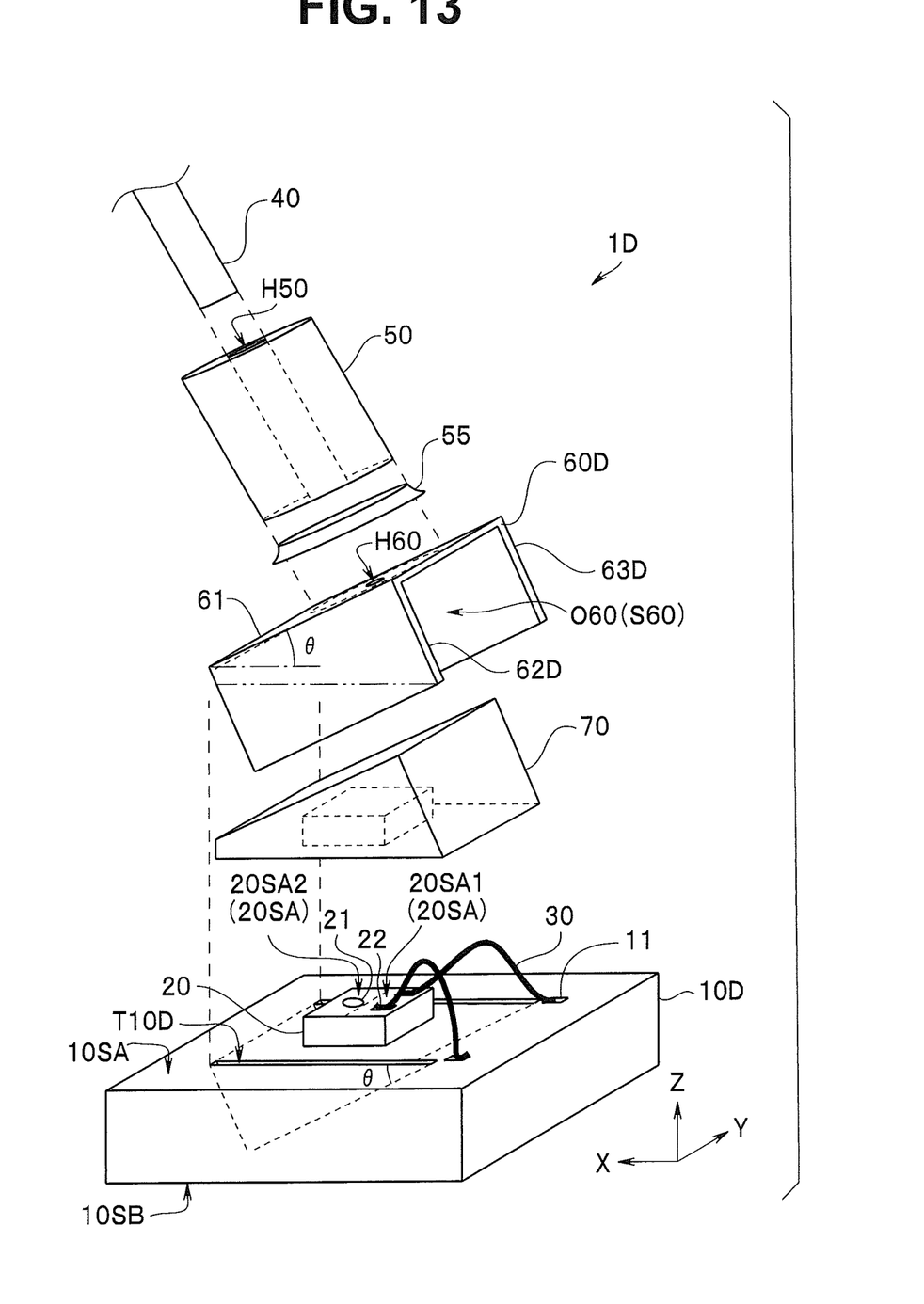
FIG. 13 is an exploded view of an optical module in an endoscope according to a fifth embodiment.

An endoscope 9D according to the present embodiment includes an optical module 1D illustrated in FIG. 13. In the optical module 1D, a position of a holding frame 60D on a first main surface 10SA is defined based on positions of grooves T10D in which side plates 62D and 63D in a holding frame 60D are respectively fitted. Not only that, an inclination angle of an upper plate 61 is defined based on a depth of the grooves T10D in which the side plates 62D and 63D are respectively inserted.

In other words, the depth of the groove T10 is constant in the optical module 1C. On the other hand, the groove T10D is inclined to the first main surface 10SA, and inclination angle θ of the groove T10D becomes an inclination angle θ of the upper plate 61.

The optical module 1D is easily manufactured because the position of the holding frame 60D and the inclination angle of the upper plate 61 are defined based on the positions and a shape of the grooves T10D.

Note that if a thickness of a wiring board 10D is small, a part of the groove T10D may be a through hole. The wiring board 10D may include at least one groove T10D.

Sixth Embodiment

Figure 14:
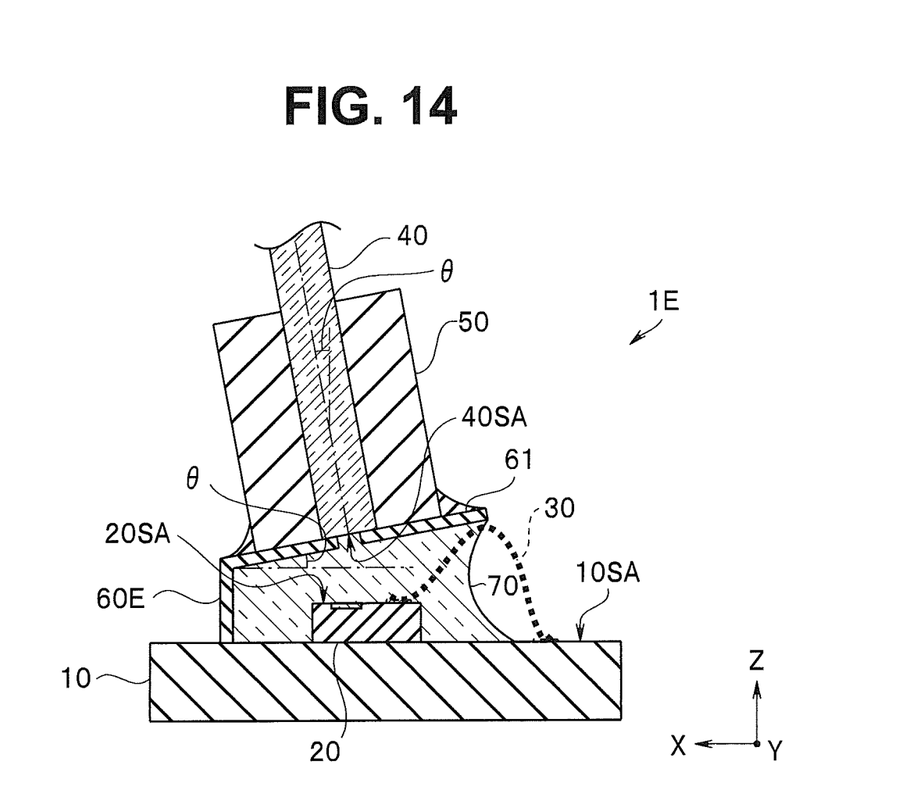
FIG. 14 is a cross-sectional view of an optical module in an endoscope according to a sixth embodiment.

An endoscope 9E according to the present embodiment includes an optical module 1E illustrated in FIG. 14. In the optical module 1E, an inclination angle θ of an upper plate 61 to a first main surface 10SA is not less than 2 degrees and not more than 12 degrees.

In the optical module 1E, a light emitting surface 20SA in an optical element 20 is inclined at an inclination angle of not less than 2 degrees and not more than 12 degrees to an end surface 40SA in an optical fiber 40. Accordingly, in the optical module 1E, multiple reflection at an interface hardly occurs, and noise does not easily occur. An endoscope 9E including the optical module 1E can display a high-quality image.

Note that an inclination angle θ of the optical fiber 40 in the optical module 1E is smaller than the inclination angle θ in the optical module 1 or the like. Accordingly, a length L90A of a distal end section 90A in the endoscope 9E is larger than the length L90A of the distal end section 90A in the endoscope 9. However, in the optical module 1E, the length L90A of the distal end section 90A is smaller than a length L90A of a distal end section 90A in an endoscope in which an inclination angle θ is zero. Thus, the endoscope 9E is more minimally invasive.

Note that in each of the above-described embodiments, the endoscope 9 including the E/O-type optical module including the light emitting element configured to convert an electric signal into an optical signal in the distal end section 90A in the insertion section 90, for example, has been described. However, the endoscope according to the embodiment may include an O/E-type optical module 1X including a light receiving element configured to convert an optical control signal into an electrical control signal to an image pickup device 2B in the distal end section 90A. The endoscope 9 may be a medical endoscope or an industrial endoscope.

The present invention is not limited to the above-described embodiments, but various modifications, combinations, and applications are possible without departing from the scope and spirit of the invention.

What is claimed is:

1. An endoscope comprising an image pickup device configured to shoot an object and output an image pickup signal and an optical module configured to convert the image pickup signal into an optical signal and transmit the optical signal using an optical fiber in a distal end section in an insertion section, wherein
the optical module comprises:
a light emitting element which includes a light emitting surface for outputting the optical signal and a rear surface, an external electrode being disposed, out of a first region and a second region obtained by dividing the light emitting surface substantially in half, only in the first region;
a wiring board which includes a first main surface and a second main surface, the light emitting element and a bonding electrode being disposed on the first main surface;
a bonding wire which connects the external electrode and the bonding electrode to each other;
a ferrule which includes an insertion hole, the optical fiber being inserted into the insertion hole;
a frame which includes an upper plate and a side plate, the ferrule being disposed on the upper plate and the side plate being fixed to the first main surface in the wiring board, and which includes an inner section housing the light emitting element and a side surface including an opening; and
a transparent resin disposed in the inner section in the frame,
wherein the upper plate is inclined at a predetermined inclination angle to the first main surface, and a first distance from the first main surface to the first region is longer than a second distance from the first main surface to the second region; and
the inclination angle is not less than 35 degrees and not more than 55 degrees.

2. The endoscope according to claim 1, wherein
the insertion section includes a bending section extending from the distal end section, and
the optical module is arranged at a position eccentric from a distal end section central axis and a position where the second region is closer to the distal end section central axis than the first region, and the optical fiber extending toward the distal end section central axis is inserted through a center of the bending section.

3. The endoscope according to claim 1, wherein the bonding wire does not contact the upper plate.

4. The endoscope according to claim 1, wherein a part of the bonding wire protrudes from the opening in the frame.

5. The endoscope according to claim 1, further comprising
a first member disposed on the first main surface in the wiring board,
wherein a position of the frame on the first main surface is defined by the first member.

6. The endoscope according to claim 1, further comprising
a second member disposed between the side plate and the first main surface,
wherein the inclination angle of the upper plate is defined by the second member.

7. The endoscope according to claim 1, further comprising
a third member disposed between the side plate and the first main surface,
wherein a position of the frame on the first main surface and the inclination angle of the upper plate are defined based on the third member.

8. The endoscope according to claim 1, wherein the first main surface in the wiring board includes a groove, and the side plate in the frame is fitted in the groove, and a position of the frame on the first main surface is defined by the groove.

9. The endoscope according to claim 8, wherein the inclination angle of the upper plate is defined by a depth of the groove into which the side plate is inserted.

10. A method for manufacturing an endoscope, the method comprising:
disposing a light emitting element on a first main surface of a wiring board, the light emitting element including a light emitting surface for outputting an optical signal and a rear surface opposing the light emitting surface, an external electrode disposed, out of a first region and a second region obtained by dividing the light emitting surface substantially in half, only in the first region, the wiring board further including a second main surface, and a bonding electrode disposed on the first main surface,
connecting the external electrode and the bonding electrode to each other with a bonding wire,
disposing a frame on the first main surface of the wiring board, the frame including an upper plate and a side plate, a side surface including an opening, the upper plate being inclined relative to the wiring board at an inclination angle to be not less than 35 degrees and not more than 55 degrees such that a first distance from the first main surface to the first region is longer than a second distance from the first main surface to the second region and the light emitting element is housed in an inner section of the frame,
disposing a ferrule on the upper plate,
inserting an optical fiber configured to transmit the optical signal into an insertion hole in the ferrule, and
injecting a transparent resin into the inner section from the opening in the frame.

* * * * *